(12) United States Patent
Teshigawara

(10) Patent No.: US 9,989,653 B2
(45) Date of Patent: Jun. 5, 2018

(54) DETECTOR, NUCLEAR MEDICAL IMAGING APPARATUS, PET-CT APPARATUS, AND PET-MRI APPARATUS

(71) Applicant: Toshiba Medical Systems Corporation, Otawara-shi (JP)

(72) Inventor: Manabu Teshigawara, Otawara (JP)

(73) Assignee: Toshiba Medical Systems Corporation, Otawara-shi (JP)

(*) Notice: Subject to any disclaimer, the term of this patent is extended or adjusted under 35 U.S.C. 154(b) by 478 days.

(21) Appl. No.: 14/834,563

(22) Filed: Aug. 25, 2015

(65) Prior Publication Data
US 2016/0054455 A1    Feb. 25, 2016

(30) Foreign Application Priority Data
Aug. 25, 2014 (JP) .................. 2014-170910

(51) Int. Cl.
| | |
|---|---|
| G01T 1/208 | (2006.01) |
| A61B 6/00 | (2006.01) |
| G01T 1/29 | (2006.01) |
| G01T 1/161 | (2006.01) |
| A61B 6/03 | (2006.01) |
| G01T 1/16 | (2006.01) |
| G01T 1/20 | (2006.01) |
| G01R 33/48 | (2006.01) |

(52) U.S. Cl.
CPC .............. *G01T 1/208* (2013.01); *A61B 6/037* (2013.01); *A61B 6/4258* (2013.01); *G01T 1/161* (2013.01); *G01T 1/1603* (2013.01); *G01T 1/2018* (2013.01); *G01T 1/2985* (2013.01); *A61B 6/032* (2013.01); *A61B 6/4417* (2013.01); *G01R 33/481* (2013.01)

(58) Field of Classification Search
CPC ..... G01T 1/208; G01T 1/1603; G01T 1/2018; G01T 1/2985; G01T 1/161; A61B 6/4258; A61B 6/037; A61B 6/032; A61B 6/4417; G01R 33/481
See application file for complete search history.

(56) References Cited

U.S. PATENT DOCUMENTS

| | | | |
|---|---|---|---|
| 7,737,404 B2* | 6/2010 | Musrock | G01T 1/2985 250/363.03 |
| 8,063,377 B2* | 11/2011 | Schulz | G01T 1/1644 250/363.04 |

(Continued)

FOREIGN PATENT DOCUMENTS

JP    2011-53130    3/2011

*Primary Examiner* — Katherine Fernandez
*Assistant Examiner* — Angela M Hoffa
(74) *Attorney, Agent, or Firm* — Oblon, McClelland, Maier & Neustadt, L.L.P.

(57) ABSTRACT

A detector of an embodiment includes a plurality of photomultipliers, a signal line, and identifying circuitry. The photomultipliers each convert light converted from radiation into an electric signal and output the electric signal. The signal line has a first path and a second path through which the electric signal passes and that have different lengths for each of the photomultipliers. The identifying circuitry identifies the photomultiplier that outputs the electric signal by a time difference between the electric signal passing through the first path and the electric signal passing through the second path.

7 Claims, 14 Drawing Sheets

(56) References Cited

U.S. PATENT DOCUMENTS

| | | | |
|---|---|---|---|
| 8,373,131 B2* | 2/2013 | Teshigawara | G01N 29/46 250/363.03 |
| 8,563,935 B2* | 10/2013 | Teshigawara | G01T 1/1611 250/363.01 |
| 8,625,868 B2* | 1/2014 | Takayama | A61B 6/037 250/362 |
| 8,937,285 B2* | 1/2015 | Kim | G01T 1/1644 250/361 R |
| 9,151,847 B2* | 10/2015 | Levin | G01T 1/164 |
| 9,176,240 B2* | 11/2015 | Gagnon | G01T 1/208 |
| 9,182,506 B2* | 11/2015 | Kim | G01T 1/2985 |
| 9,194,959 B2* | 11/2015 | Schmand | G01T 1/1642 |
| 9,239,393 B2* | 1/2016 | Teshigawara | G01T 1/2985 |
| 9,271,694 B2* | 3/2016 | Kim | A61B 6/037 |
| 9,513,378 B2* | 12/2016 | Roknsharifi | G01T 1/1647 |
| 9,575,192 B1* | 2/2017 | Ng | G01T 1/20 |
| 9,625,588 B2* | 4/2017 | Frisch | G01T 1/208 |
| 2009/0072153 A1* | 3/2009 | Musrock | G01T 1/2985 250/363.03 |
| 2010/0038546 A1* | 2/2010 | Schulz | G01T 1/1644 250/362 |
| 2011/0064293 A1* | 3/2011 | Takayama | A61B 6/037 382/131 |
| 2012/0312996 A1* | 12/2012 | Teshigawara | G01N 29/46 250/363.03 |
| 2013/0009067 A1* | 1/2013 | Schmand | G01T 1/1642 250/363.03 |
| 2013/0134314 A1* | 5/2013 | Teshigawara | G01T 1/2985 250/363.03 |
| 2013/0151800 A1* | 6/2013 | Teshigawara | G01T 1/1611 711/159 |
| 2013/0299707 A1* | 11/2013 | Levin | G01T 1/164 250/363.03 |
| 2013/0334428 A1* | 12/2013 | Kim | G01T 1/1644 250/363.03 |
| 2014/0021354 A1* | 1/2014 | Gagnon | G01T 1/1647 250/362 |
| 2015/0001403 A1* | 1/2015 | Kim | G01T 1/2985 250/363.03 |
| 2015/0168567 A1* | 6/2015 | Kim | A61B 6/037 250/370.11 |
| 2015/0285922 A1* | 10/2015 | Mintzer | G01T 1/208 600/411 |
| 2016/0041277 A1* | 2/2016 | Roknsharifi | G01T 1/1647 250/371 |

\* cited by examiner

FIG.2

| MODULE ID | SCINTILLATOR NUMBER (P) | ENERGY VALUE (E) | DETECTION TIME (T) |
|---|---|---|---|
| D1 | P11 | E11 | T11 |
|  | P12 | E12 | T12 |
|  | P13 | E13 | T13 |
|  | ⋮ | ⋮ | ⋮ |

| MODULE ID | SCINTILLATOR NUMBER (P) | ENERGY VALUE (E) | DETECTION TIME (T) |
|---|---|---|---|
| D2 | P21 | E21 | T21 |
|  | P22 | E22 | T22 |
|  | P23 | E23 | T23 |
|  | ⋮ | ⋮ | ⋮ |

| MODULE ID | SCINTILLATOR NUMBER (P) | ENERGY VALUE (E) | DETECTION TIME (T) |
|---|---|---|---|
| D3 | P31 | E31 | T31 |
|  | P32 | E32 | T32 |
|  | P33 | E33 | T33 |
|  | ⋮ | ⋮ | ⋮ |

| COINCIDENCE NO. | SCINTILLATOR NUMBER (P) | ENERGY VALUE (E) | DETECTION TIME (T) | SCINTILLATOR NUMBER (P) | ENERGY VALUE (E) | DETECTION TIME (T) |
|---|---|---|---|---|---|---|
| 1 | P11 | E11 | T11 | P22 | E22 | T22 |
| 2 | P12 | E12 | T12 | P32 | E32 | T32 |
| 3 | P13 | E13 | T13 | P33 | E33 | T33 |
| ... | ... | ... | ... | ... | ... | ... |

US 9,989,653 B2

DETECTOR, NUCLEAR MEDICAL IMAGING APPARATUS, PET-CT APPARATUS, AND PET-MRI APPARATUS

CROSS-REFERENCE TO RELATED APPLICATION

This application is based upon and claims the benefit of priority of the prior Japanese Patent Application No. 2014-170910, filed on Aug. 25, 2014, the entire contents of which are incorporated herein by reference. The entire contents of the prior Japanese Patent Application No. 2015-155979, filed on Aug. 6, 2015, are also incorporated herein by reference.

FIELD

Embodiments described herein relate generally to a detector, a nuclear medical imaging apparatus, a positron emission tomography-computed tomography (PET-CT) apparatus, and a positron emission tomography-magnetic resonance imaging (PET-MRI) apparatus.

BACKGROUND

A positron emission tomography (PET) apparatus has been known as a nuclear medical imaging apparatus that can perform functional diagnosis in living tissue of subjects.

In imaging by the PET apparatus, for example, first, a subject is administered with a radioactive pharmaceutical labeled with a positron emission nuclide. The positron emission nuclide selectively captured into living tissue within the subject emits positrons, and the emitted positrons combine with electrons, undergo pair annihilation, and emit a pair of gamma rays in substantially opposite directions. The PET apparatus detects the gamma rays using detectors arranged around the subject in a ring shape and generates coincidence counting information (a coincidence list) from the detection result. The PET apparatus generates a PET image by reconstruction using the generated coincidence counting information.

The detector of the nuclear radical imaging apparatus such as the PET apparatus includes, for example, a scintillator and a photomultiplier. The scintillator converts a gamma ray emitted from internal tissue within a subject into light having a peak in the ultraviolet region and outputs the light. The photomultiplier converts the light output from the scintillator into an electric signal.

Recently detectors using a SiPM as the photomultiplier have practically been utilized. In such a detector, a SiPM is installed for each scintillator, and reading channel is assigned to each SiPM, thus leading to an enormous number of reading channels.

BRIEF DESCRIPTION OF THE DRAWINGS

FIG. 2 is a diagram for illustrating a list of counting information in the embodiment;

FIG. 3 is a diagram for illustrating a time-series list of coincidence counting information in the embodiment;

DETAILED DESCRIPTION

A detector of an embodiment includes a plurality of photomultipliers, a signal line, and identifying circuitry. The photomultipliers each convert light converted from radiation into an electric signal and output the electric signal. The signal line has a first path and a second path through which the electric signal passes and that have different lengths for each of the photomultipliers. The identifying circuitry identifies the photomultiplier that outputs the electric signal by a time difference between the electric signal passing through the first path and the electric signal passing through the second path.

The following describes embodiments of the detector and a nuclear medical imaging apparatus in detail with reference to the attached drawings.

Embodiments

The following first describes a configuration of nuclear medical imaging apparatus according to the embodiment. The embodiment describes a PET apparatus as an example of the nuclear medical imaging apparatus.

Figure 1:
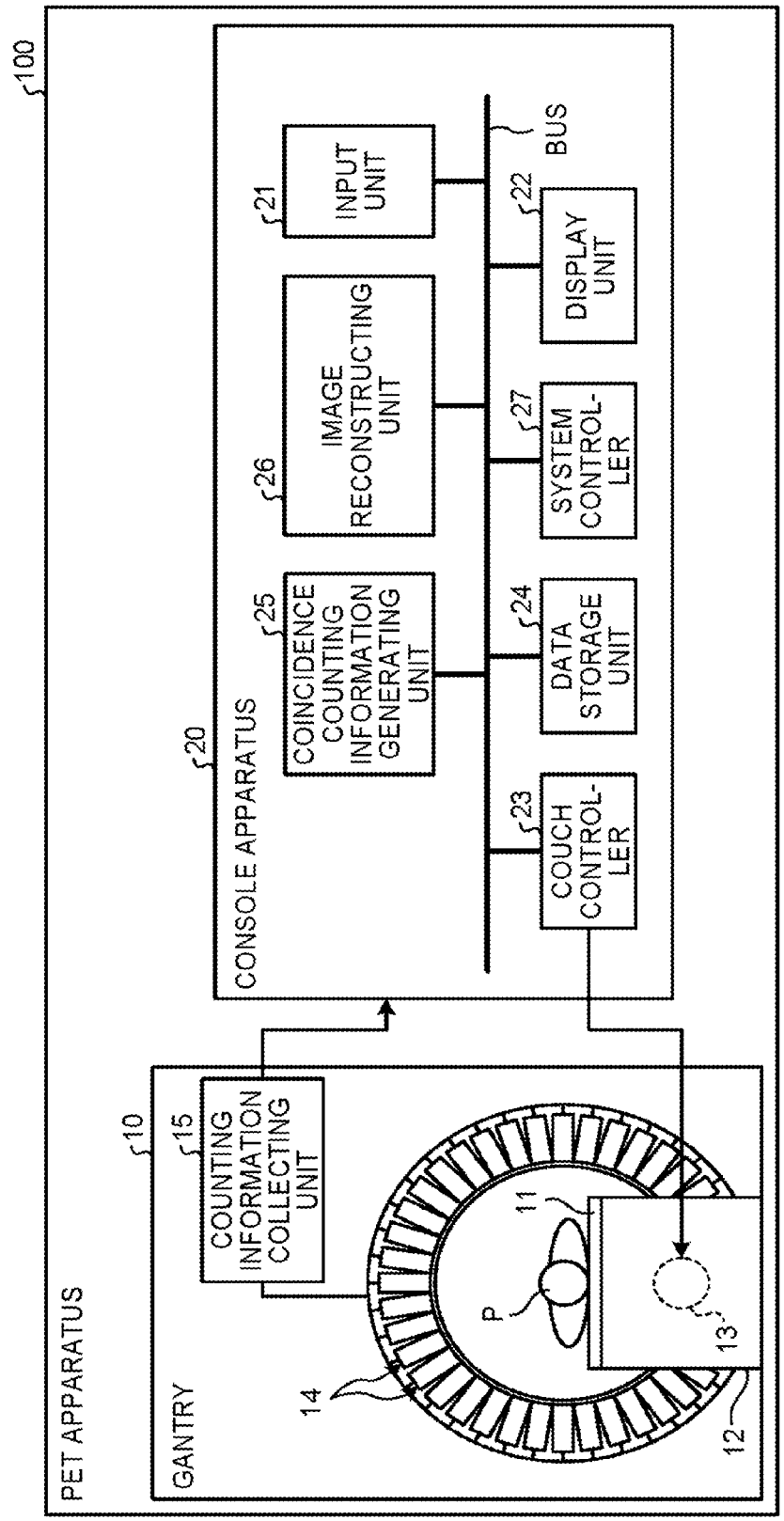
FIG. 1 is a block diagram illustrating an example of a configuration of a PET apparatus according to an embodiment.

FIG. 1 is a block diagram illustrating an example of a configuration of a PET apparatus 100 according to the embodiment. As illustrated in FIG. 1, the PET apparatus 100 according to the embodiment includes a gantry 10 and a console apparatus 20.

The gantry 10 detects a pair of gamma rays (pair annihilation gamma rays) emitted when positrons emitted within a subject P combine with electrons and undergo pair annihilation by detector modules arranged so as to surround the subject P in a ring shape and generates counting information from output signals of the detector modules, thereby collecting the counting information. The subject P is administered with, for example, a radioactive pharmaceutical labeled with a positron emission nuclide. Gamma rays are an example of radiation.

As illustrated in FIG. 1, the gantry 10 includes couchtop 11, a couch 12, a couch drive unit 13, a plurality of detector modules 14, and a counting information collecting unit 15. As illustrated in FIG. 1, the gantry 10 has a cavity serving as an imaging port.

The couchtop 11 is a bed on which the subject P is mounted and is arranged on the couch 12. The couch drive unit 13 moves the couchtop 11 under the control of a couch controller 23 described below. The couch drive unit 13, for example, moves the couchtop 11, thereby moving the subject P into the imaging port of the gantry 10.

The detector modules 14 detect the gamma rays emitted from within the subject P. As illustrated in FIG. 1, the detector modules 14 are arranged so as to surround the subject P in a ring shape. The detector modules 14 convert the gamma rays emitted from within the subject P into light and covert the converted light into electric signals. The configuration of the detector module 14 will be described below. The detector module 14 is an example of the detector.

The counting information collecting unit 15 generates counting information from the output signals of the detector modules 14 and stores the generated counting information in a data storage unit 24 described below.

The counting information collecting unit 15, for example, generates the counting information from the output signals of the detector modules 14, thereby collecting the counting information. The counting information contains a detection position, an energy value, and a detection time of a gamma ray. As described below, for example, the counting information contains a scintillator number (P), an energy value (E), and a detection time (T). Although not illustrated in FIG. 1, the detector modules 14 are sectioned into a plurality of blocks, and the counting information collecting unit 15 is provided for each block. When one detector module 14 forms one block, for example, the counting information collecting unit 15 is provided for each detector module 14. The counting information collecting unit 15 will be described below.

The console apparatus 20 receives operation on the PET apparatus 100 by an operator, controls imaging of PET images, and reconstructs PET images using the counting information collected by the gantry 10. As illustrated in FIG. 1, the console apparatus 20 includes an input unit 21, a display unit 22, the couch controller 23, the data storage unit 24, a coincidence counting information generating unit 25, an image reconstructing unit 26, and a system controller 27. The units included in the console apparatus 20 are connected to each other via a bus.

The input unit 21 is a mouse, a keyboard, or the like for use in input of various kinds of instructions and various kinds of settings by the operator of the PET apparatus 100 and transfers the input various kinds of instructions and various kind of settings to the system controller 27. The input unit 21 is, for example, used for input of an imaging starting instruction. The display unit 22 is a monitor or the like referred to by the operator and displays PET images and a graphical user interface (GUI) for receiving various kinds of instructions and various kinds of settings from the operator under the control of the system controller 27. The couch controller 23 controls the couch drive unit 13.

The data storage unit 24 stores therein various van us kinds of data used in the PET apparatus 100. The data storage unit 24 is implemented by, for example, a semiconductor memory device such as a random access memory (RAM) and a flash memory, a hard disk, or an optical disc.

The data storage unit 24 stores therein a list of the counting information generated by the respective counting information collecting units 15. The list of the counting information stored in the data storage unit 24 is used for processing by the coincidence counting information generating unit 25. The list of the counting information stored in the data storage unit 24 may be deleted after being used in the processing by the coincidence counting information generating unit 25 or stored for a certain period of time.

FIG. 2 is a diagram for illustrating the list of the counting information in the embodiment. As illustrated in FIG. 2, the data storage unit 24 stores therein the counting information containing the scintillator number (P), the energy value (E), and the detection time (T) in association with a module ID that identifies the detector module 14.

The data storage unit 24 stores therein a time-series list of coincidence counting information generated by the coincidence counting information generating unit 25. The time-series list of the coincidence counting information stored in the data storage unit 24 is used for processing by the image reconstructing unit 26. The time-series list of the coincidence counting information stored in the data storage unit 24 may be deleted after being used in the processing by the image reconstructing unit 26 or stored for a certain period of time.

FIG. 3 is a diagram for illustrating the time-series list of the coincidence counting information in the embodiment. As illustrated in FIG. 3, the data storage unit 24 stores therein groups of the counting information in association with a coincidence No. as a serial number of the coincidence counting information. In the embodiment, the time-series list of the coincidence counting information is arranged generally on a time-series basis based on the detection time (T) of the counting information.

The data storage unit 24 stores therein the PET images reconstructed by the image reconstructing unit 26. PET images stored in the data storage unit 24 are displayed on the display unit 22 by the system controller 27.

Referring back to FIG. 1, the coincidence counting information generating unit 25 generates the time-series list of the coincidence counting information using the list of the counting information generated by the counting information collecting unit 15. The coincidence counting information generating unit 25, for example, searches the list of the counting information stored in the data storage unit 24 for a group of the counting information that has counted a pair of gamma rays substantially simultaneously based on the detection time (T) of the counting information. The coincidence counting information generating unit 25 generates the coincidence counting information for each group of the counting information searched for and stores the generated coincidence counting information in the data storage unit 24 while arranging the information generally on a time-series basis.

The coincidence counting information generating unit 25, for example, generates the coincidence counting information based on a condition (a coincidence counting information generation condition) when generating the coincidence counting information input by the operator. The coincidence counting information generation condition designates a time window width. The coincidence counting information generating unit 25, for example, generates the coincidence counting information based on the time window width.

The coincidence counting information generating unit 25, for example, refers to the data storage unit 24 and searches the detector modules 14 for a group of the counting information the time difference of the detection times (T) of which is within the time window width. When the coincidence counting information generating unit 25, for example, searches for a group of "P11, E11, T11" and "P22, E22, T22" as a group satisfying the coincidence counting information generation condition, the coincidence counting information generating unit 25 generates this group as the coincidence counting information and stores the coincidence counting information in the data storage unit 24. The coincidence counting information generating unit 25 may generate the coincidence counting information using an energy window width together with the time window width. The coincidence counting information generating unit 25 may be provided within the gantry 10.

The image reconstructing unit 26 reconstructs PET images. The image reconstructing unit 26, for example, reads the time-series list of the coincidence counting information stored in the data storage unit 24 and reconstructs the PET images using the read time-series list. The image reconstructing unit 26 stores the reconstructed PET images in the data storage unit 24.

The system controller 27 controls the gantry 10 and the console apparatus 20, thereby controlling the entire PET apparatus 100. The system controller 27, for example, controls imaging in the PET apparatus 100. The respective units, that is, the coincidence counting information generating unit 25, the image reconstructing unit 26, and the system controller 27 are implemented by an integrated circuit such as an application specific integrated circuit (SIC) and a field programmable gate array (FPGA) and an electronic circuit such as a central processing unit (CPU) and a micro processing unit (MPU).

The entire configuration of the PET apparatus according to the embodiment has been described. With the configuration, the PET apparatus according to the embodiment identifies a scintillator that has converted light converted from a gamma ray into an electric signal as described below.

Figure 4A:
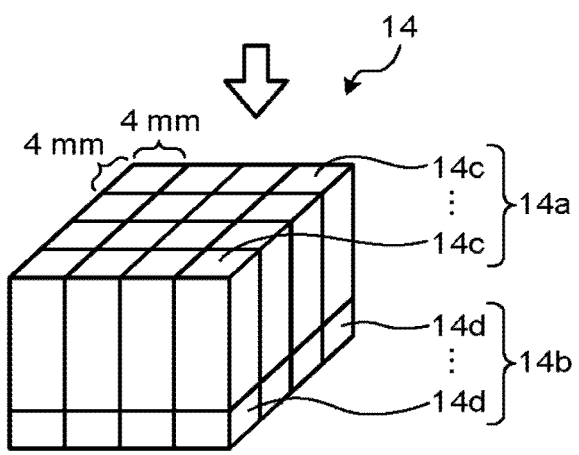
FIG. 4A is a diagram illustrating an example of a configuration of a detector module.

The following first describes an example of a configuration of the detector module 14. FIG. 4A is a diagram illustrating the example of the configuration of the detector module 14. As illustrated in FIG. 4A, the detector module 14 includes a scintillator array 14a and a SiPM array 14b.

The scintillator array 14a includes a plurality of scintillators 14c arranged in a two-dimensional manner. The scintillator 14c converts a gamma ray emitted from internal tissue of the subject P into light having a peak in the ultraviolet region and outputs the light. When the top face of the scintillator 14c is regarded as a quadrangle, the top face of the scintillator 14c has size of, for example, 4×4 mm as illustrated in FIG. 4A.

The SiPM array 14b includes a plurality of SiPMs 14d arranged in a two-dimensional manner. The respective SiPMs 14d are optically coupled to the respective scintillators 14c. The SiPM 14d converts the light output from the optically coupled scintillator 14c into an electric signal and outputs the electric signal. The SiPM 14d amplifies light as an electric signal with a certain gain rate. The SiPM 14d is an example of the photomultiplier.

Figure 4B:
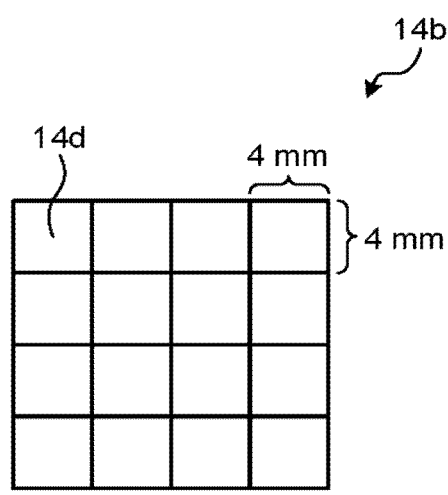
FIG. 4B is a diagram illustrating an example when a SiPM array is viewed from the arrow direction in FIG. 4A.

FIG. 4B is a diagram illustrating an example when the SiPM array 14b viewed from the arrow direction in FIG. 4A. When the top face of the SiPM 14d is regarded as a quadrangle, the top face of the SiPM 14d has a size of, for example, 4×4 mm as illustrated in FIG. 4B.

The SiPM 14d includes a plurality of avalanche photodiodes (APDs) (not illustrated) arranged in a two-dimensional manner, and these APD converts the light emitted from the scintillator 14c into the electric signal. The APD amplifies light as an electric signal with a certain gain rate. Electric signals output from the APDs arranged in a two-dimensional manner are combined to form the electric signal output from the SiPM 14d.

In the present embodiment, the SiPMs 14d are divided into a plurality of groups. As illustrated in FIG. 4B, for example, one detector module 14 contains 16 SiPMs 14d, and when four SiPMs 14d are regarded a one group, the SiPMs 14d in one detector module 14 are divided into four groups. The following describes a case in which four SiPMs 14d are regarded as one group, two or more, other than four, SiPMs 14d may be regarded as one group.

Figure 5:
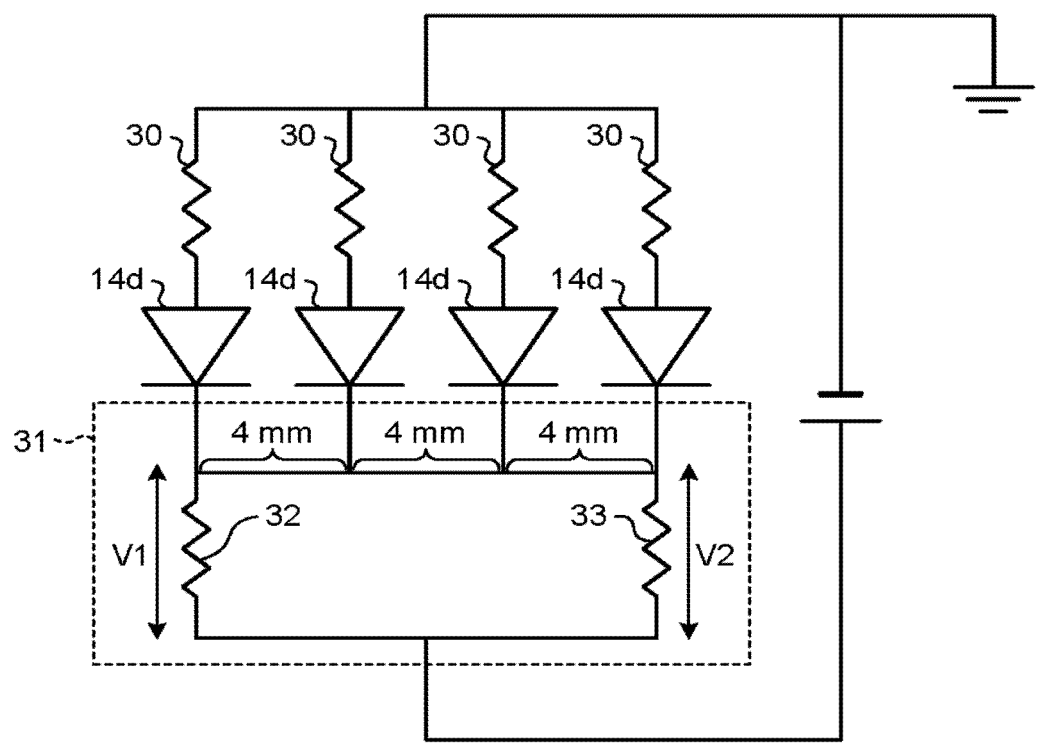
FIG. 5 is a diagram illustrating an example of electric connection relation of SiPMs in one group.

FIG. 5 is a diagram illustrating an example of electric connection relation the SiPMs 14d in one group. As exemplified in FIG. 5, the four SiPMs 14d in one group are connected in parallel. In FIG. 5, a resistor 30 collectively represents quenching resistors coupled to the respective APDs contained in the SiPM 14d. As illustrated in FIG. 5, voltage of a yield voltage or more for an element to operate at the Geiger mode is applied to the respective APDs contained in the SiPMs 14d.

As illustrated in FIG. 5, a signal line 31 is connected to the four SiPMs 14d in one group. The signal line 31 has a first path and a second path having different lengths through which an electric signal passes for each SiPM 14d.

The following describes the first path and the second path. The first path is a path in which the electric signal output from the SiPM 14d passes through a resistor 32. The second path is a path in which the electric signal output from the SiPM 14d passes through a resistor 33. The resistance of the resistor 32 and the resistance of the resistor 33 are the same. Below, a voltage across both ends of the resistor 32 is written as "V1," whereas a voltage across both ends of the resistor 3 is written as "V2."

The distance between the four SiPMs 14d arranged in parallel is a predetermined value. In the example in FIG. 5, for example, the distance between the SiPMs 14d arranged in parallel is 4 mm. Although the following describes a case in which the distance between the SiPMs 14d is 4 mm cited as an example, the distance between the SiPMs 14d can be any value. The distance between the SiPMs 14d can be, for example, 12 mm. The distance between the SiPMs 14d arranged in parallel is 4 mm, and in the example in FIG. 5, there is a difference of 12 mm between the path length from the leftmost SiPM 14d to the resistor 32 and the path length from the leftmost SiPM 14d to the resistor 33. In other words, as to the first path and the second path, the second path is longer by 12 mm.

In the example in FIG. 5, there is a difference of 4 mm between the path length from the second leftmost SiPM 14d to the resistor 32 and the path length from the second leftmost SiPM 14d to the resistor 33. In other words, as to the first path and the second path, the second path is longer by 4 mm.

In the example in FIG. 5, there is difference of 4 mm between the path length from the second rightmost SiPM 14d to the resistor 3 and the path length from the second rightmost SiPM 14d to the resistor 33. In other words, as to the first path and the second path, the first path is longer by 4 mm.

In the example in FIG. 5, there is a difference of 12 mm between the path length from the rightmost SiPM 14d to the resistor 32 and the path length from the rightmost SiPM 14d to the resistor 33. In other words, as to the first path and the second path, the first path is longer by 12 mm.

In the example in FIG. 5, when the light output from the scintillator 14c is made incident on the leftmost SiPM 14d, the leftmost SiPM 14d converts the light made incident thereon into an electric signal and outputs the electric signal to the signal line 31. Considering that as to the first path and the second path, the second path is longer by 12 mm, when it takes 10 ps for the electric signal to travel by 3 mm, an electric signal of "V2" rises 40 ps after an electric signal of "V1" rises. In other words, a time from when the electric signal of "V1" rises to when the electric signal of "V2" rises is 40 ps.

In the example in FIG. 5, when the light output from the scintillator 14c is made incident on the second leftmost SiPM 14d, the second leftmost SiPM 14d convert the light made incident thereon into an electric signal and outputs the electric signal to the signal line 31. Considering that as to the first path and the second path, the second path is longer by 4 mm, when it takes 12 ps for the electric signal to travel by 3 mm, the electric signal of "V2" rises 13.33 ps after the electric signal of "V1" rises. In other words, the time from when the electric signal of "V1" rises to when the electric signal of "V2" rises is 13.33 ps.

In the example in FIG. 5, when the light output from the scintillator 14c is made incident on the second rightmost SiPM 14d, the second rightmost SiPM 14d converts the light made incident thereon into an electric signal and outputs the electric signal to the signal line 31. Considering that as to the first path and the second path, the first path is longer by 4 mm, when it takes 10 ps for the electric signal to travel by a 3 mm, the electric signal of "V1" rises 13.33 ps after the electric signal of "V2" rises. In other words, the time from when the electrical signal of "V2" rises to when the electric signal of "V1" rises is 13.33 ps.

In the example in FIG. 5, when the light output from the scintillator 14c is made incident on the rightmost STEM 14d, the rightmost SiPM 14d converts the light made incident thereon into an electric signal and outputs the electric signal to the signal line 31. Considering that as to the first path and the second path, the first path is longer by 12 mm, when it takes 10 ps for the electric signal to travel by 3 mm, the electric signal of "V1" rises 40 ps after the electric signal of "V2" rises. In other words, the time from when the electric signal of "V2" rises to when the electric signal of "V1" rises is 40 ps.

Figure 6:
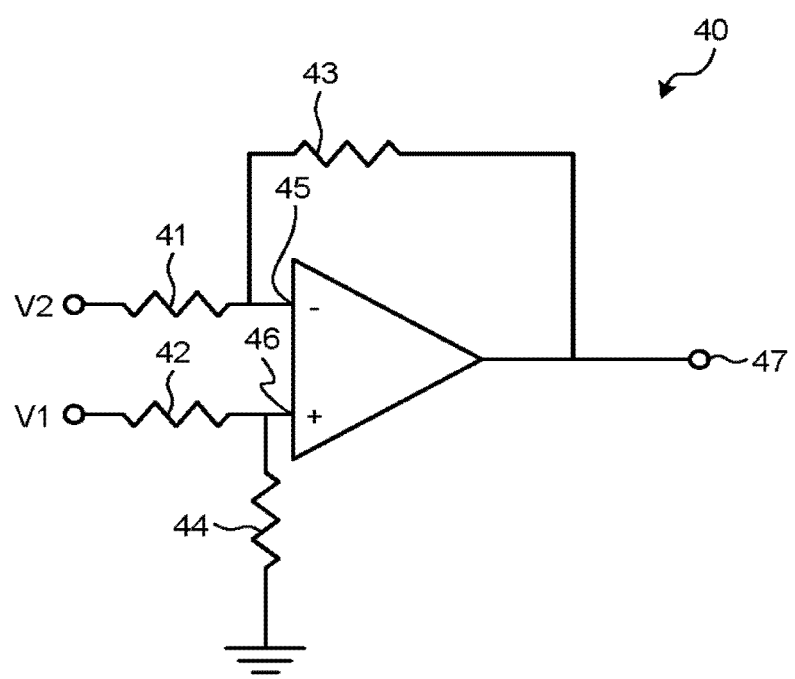
FIG. 6 is a diagram illustrating an example of a differential amplifier circuit.

In the embodiment, a plurality of SiPMs 14d are regarded as one group, and for each group, a differential amplifier circuit is provided that outputs a differential signal indicating a difference between the electric signal passing through the first path and the electric signal passing through the second path, the difference signal indicating a time difference in timing at which the electric signal passes between the first path and the second path. FIG. 6 is a diagram illustrating an example of a differential amplifier circuit 40. As illustrated in FIG. 6, the differential amplifier circuit 40 and the signal line 31 are connected so that the electric signal of "V2" input to an inverting input terminal 45 of the differential amplifier circuit 40, whereas the electric signal of "V1" is input to a non-inverting input terminal 46.

In FIG. 6, a resistance R1 of a resistor 41 and a resistance R2 of a resistor 42 are the same, whereas a resistance R3 of a resistor 43 and a resistance R4 of a resistor 44 are the same. An electric signal with an output voltage represented by "(V1−V2)R3/R1" is output from an output terminal 47 of the differential amplifier circuit 40. The electric signal with the output voltage represented by "(V1−V2)R3/R1" is an example of a differential signal indicating a difference between the electric signal of "V1" and the electric signal of "V2," the differential signal indicating a time difference between timing at which the electric signal of "V1" passes through the resistor 32 and timing at which the electric signal of "V2" passes through the resistor 33. The output terminal 47 is connected to the counting information collecting unit 15, and the electric signal with the output voltage represented by "(V1−V2)R3/R1" input to the counting information collecting unit 15. Although the following describes a case in which the resistance R1, the resistance R2, the resistance R3, and the resistance R4 are the same, the resistance R1, the resistance R2, the resistance R3, and the resistance R4 may be different from each other.

Figure 7:
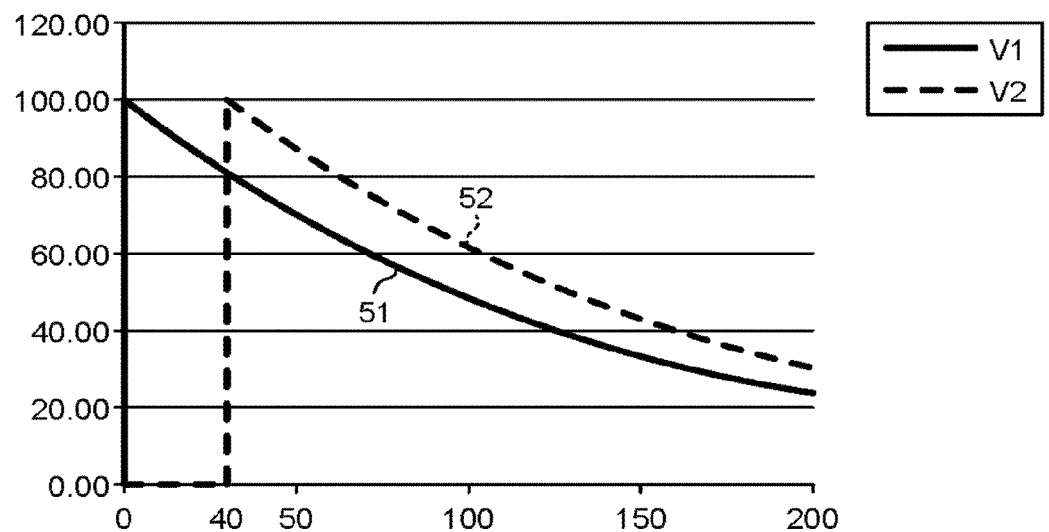
FIG. 7 is a diagram illustrating examples of waveforms of an electric signal of "V1" and an electric signal of "V2"

FIG. 7 is a diagram illustrating examples of waveforms of the electric signal of "V1" and the electric signal of "V2." In the example in FIG. 7, the horizontal axis indicates time [ps], whereas the vertical axis indicates voltage value [V]. The example in FIG. 7 illustrates a waveform 51 of the electric signal of "V1" and a waveform 52 of the electric signal of "V2." As illustrated by the waveform 51 of the electric signal of "V1" and the waveform 52f the electric signal of "V2," the electric signal of "V2" rises 40 ps after the electric signal of "V1" rises. In other words, the example in FIG. 7 illustrates a case in which the leftmost SiPM 14d in the example in FIG. 5 has converted the light made incident thereon into the electric signal and has output the electric signal to the signal line 31.

Figure 8:
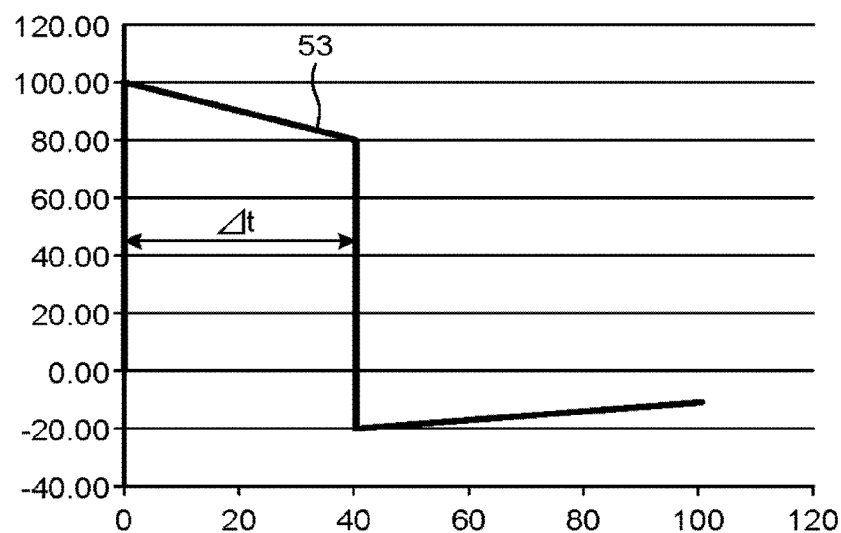
FIG. 8 is a diagram illustrating an example a waveform of an electric signal output from an output terminal.

When the electric signal of "V1" indicated by the waveform 51 is input to the non-inverting input terminal 46, and the electric signal of "V2" indicated by the waveform 52 is input to the inverting input terminal 45, the electric signal with the output voltage represented by "(V1−V2)R3/R1" indicated by a waveform 53 in FIG. 8 is output from the output terminal 47. FIG. 8 is a diagram illustrating example of a waveform of the electric signal output from the output terminal 47. Also in the example in FIG. 8, the horizontal axis indicates time [ps], whereas the vertical axis indicates voltage value [V]. Δt in the example in FIG. 8 indicates a time from a rise of the electric signal indicated by the waveform 53 to a fall thereof. The electric signal of "V2" rises 40 ps after the electric signal of "V1" rises, and the Δt in the example in FIG. 8 is 40 ps.

When the electric signal of "V1" and the electric signal of "V2," in which the electric signal of "V2" rises 13.33 ps after the electric signal of "V1" rises, are input to the non-inverting input terminal 46 and the inverting input terminal 45, respectively, a time from the rise to the fall of the electric signal output from the output terminal 47 is 13.33 ps.

When the electric signal of "V2" and the electric signal of "V2," in which the electric signal of "V1" rises 13.33 ps after the electric signal of "V2" rises, are input to the non-inverting input terminal 46 and the inverting input terminal 45, respectively, the time from the fall to the rise of the electric signal output from the output terminal 47 is 13.33 ps.

When the electric signal of "V1" and the electric signal of "V2," in which the electric signal of "V1" rises 40 ps after the electric signal of "V2" rises, are input to the non-inverting input terminal 46 and the inverting input terminal 45, respectively, the time from the fall to the rise of the electric signal output from the output terminal 47 is 40 ps.

As described above, in one group, the order of the rise of the respective electric signals of the electric signal of "V1" and the electric signal of "V2" and the time between the rise of the electric signal of "V1" and the rise of the electric signal of "V2" are unique to each SiPM 14d. Given this situation, using these pieces of unique information, the SiPM 14d that has output the electric signal can be identified, and further the scintillator 14c optically coupled to the SiPM 14d that has output the electric signal can also be identified. In other words, using these pieces of unique information can identify the scintillator 14c on which the gamma ray has been made incident. The example in FIG. 5 describes a case in which the SiPMs 14d in each group are arranged at regular intervals. However, when the order of the rise of the respective electric signals of the electric signal of "V1" and the electric signal of "V2" and the time between the rise of the electric signal of "V1" and the rise of the electric signal of "V2" are unique for each group, the SiPMs 14d in each group are not required to be arranged at regular intervals. In the example in FIG. 5, for example, when the number of groups is an odd number, and the SiPMs 14d in each group are arranged at regular intervals, as to the SiPM 14d of the group positioned at the middle, the lengths of the first path and the second path may be the same. In this case, the temporal difference between the rise of the electric signal of "V1" and the rise of the electric signal of "V2" output from the SiPM 14d of the group positioned at the middle disappears. For this reason, even when the SiPM 14d of the group positioned at the middle outputs the electric signal, it may be difficult to identify this SiPM 14d. In such a case, the arrangement of the SiPMs 14d of the group positioned at the middle may be displaced to make the lengths of the first path and the second path different from each other.

The differential amplifier circuit provided for each group is not limited to the differential amplifier circuit 40 illustrated in FIG. 6, and any circuit can be employed that outputs a differential signal indicating a difference between the electric signal passing through the first path and the electric signal passing through the second path, the difference signal indicating a time difference in timing at which the electric signal passes between the first path and the second path.

Figure 9:
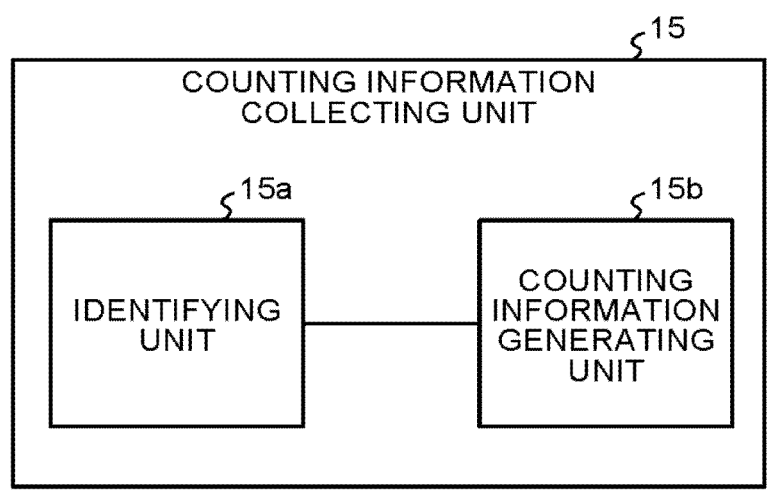
FIG. 9 is a diagram illustrating an example a functional configuration of a counting information collecting unit.

The following describes an example of a functional configuration of the counting information collecting unit 15. FIG. 9 is a diagram illustrating the example of the functional configuration of the counting information collecting unit 15. As illustrated in the example in FIG. 9, the counting information collecting unit 15 includes an identifying unit 15a and a counting information generating unit 15b.

The identifying unit 15a, based on the electric signal output from the differential amplifier circuit 40, identifies the scintillator 14c that has output light corresponding to the electric signal output from the differential amplifier circuit 40 from among the scintillators 14c. The identifying unit 15a identifies the SiPM 14d that outputs an electric signal by the time different between the electric signal passing through the first path and the electric signal passing through the second path.

When the identifying unit 15a receives an electric signal containing such a pulse as to rise and then fall or such a pulse as to fall and then rise from the differential amplifier circuit 40, for example, the identifying unit 15a determines a time Δt between the rise and the fall of the pulse.

When the determined time Δt 40 ps, and when the pulse contained in the electric signal received from the differential amplifier circuit 40 is such a pulse as to rise and then fall, the identifying unit 15a identifies the leftmost SiPM 14d as the SiPM that has output the electric signal from among the four SiPMs 14d in the example in FIG. 5.

When the determined time Δt is 13.33 ps, and when the pulse contained in the electric signal received from the differential amplifier circuit 40 is such a pulse as to rise and then fall, the identifying unit 15a identifies the second leftmost SiPM 14d as the SiPM that has output the electric signal from among the four SiPMs 14d in the example in FIG. 5.

When the determined time Δt is 13.33 ps, and when the pulse contained in the electric signal received from the differential amplifier circuit 40 is such a pulse as to fall and then rise, the identifying unit 15a identifies the second rightmost SiPM 14d as the SiPM that has output the electric signal from among the four SiPMs 14d in the example in FIG. 5.

When the determined time Δt is 40 ps, and when the pulse contained in the electric signal received from the differential amplifier circuit 40 is such a pulse as to fall and then rise, the identifying unit 15a identifies the rightmost SiPM 14d as the SiPM that has output the electric signal from among the four SiPMs 14d in the example in FIG. 5.

When the SiPM 14d has been identified, the identifying unit 15a identifies the scintillator 14c optically coupled to the identified SiPM 14d as the scintillator that has output the light corresponding to the electric signal output from the differential amplifier circuit 40.

By the above method, the identifying unit 15a identifies the scintillator 14c that has output the light corresponding to the electric signal output from the differential amplifier circuit 40 from among the scintillators 14c.

The counting information generating unit 15b generates the counting information. The counting information generating unit 15b, for example, identifies the scintillator number (P) indicating the position of the scintillator 14c identified by the identifying unit 15a. The counting information generating unit 15b, based on the electric signal output from the differential amplifier circuit 40, calculates the intensity of the electric signal output from the scintillator 14c identified by the identifying unit 15a and integrates the calculated intensity, thereby determining the energy value (E) of the gamma ray made incident on the detector module 14. The counting information generating unit 15b determines the detection time (T) when the gamma ray has been detected by the detector module 14. The counting information generating unit 15b, for example, determines the detection time (T) with an accuracy down to $10^{-12}$ seconds (picoseconds). The detection time (T) may be absolute time or a time elapsed from a point of time of starting imaging. The counting information generating unit 15b then generates the counting information containing the scintillator number (P), the energy value (E), and the detection time (T).

As described above, in the present embodiment, based on the electric signal output from the output terminal 47 of the differential amplifier circuit 40 provided for each group, the scintillator 14c on which the gamma ray has been made incident is identified, and the counting information is generated. It follows that in the present embodiment when the number of all scintillators 14c is "Nmax" and the number of the SiPMs 14d contained in one group is "Ngroup," the number of reading channels can be "Nmax/Ngroup."Consequently, the detector module 14 and the PET apparatus 100 according to the present embodiment can reduce an increase in the number of the reading channels.

The following describes a case in which one SiPM is assigned to one scintillator and a reading circuit for reading an electric signal output from the SiPM is assigned to one SiPM in a detector of a PET apparatus. The detector of the PET apparatus is shaped in a cylindrical form surrounding a subject. The diameter of the cylindrical detector is about 800 mm, and the detector has a length of about 200 mm in the body axis direction. When a light-receiving face of the SiPM has a size of 4 mm×4 mm, the number of the SiPMs constituting the detector is 31,400, which also requires 31,400 reading circuits. The number of the reading channels thus becomes enormous when the reading circuit for reading an electric signal output from the SiPM is assigned to one SiPM.

In contrast, as described above, in the present embodiment, the number of the reading channels can be "Nmax/Ngroup," and an increase in the number of the reading channels can be reduced.

Figure 10:
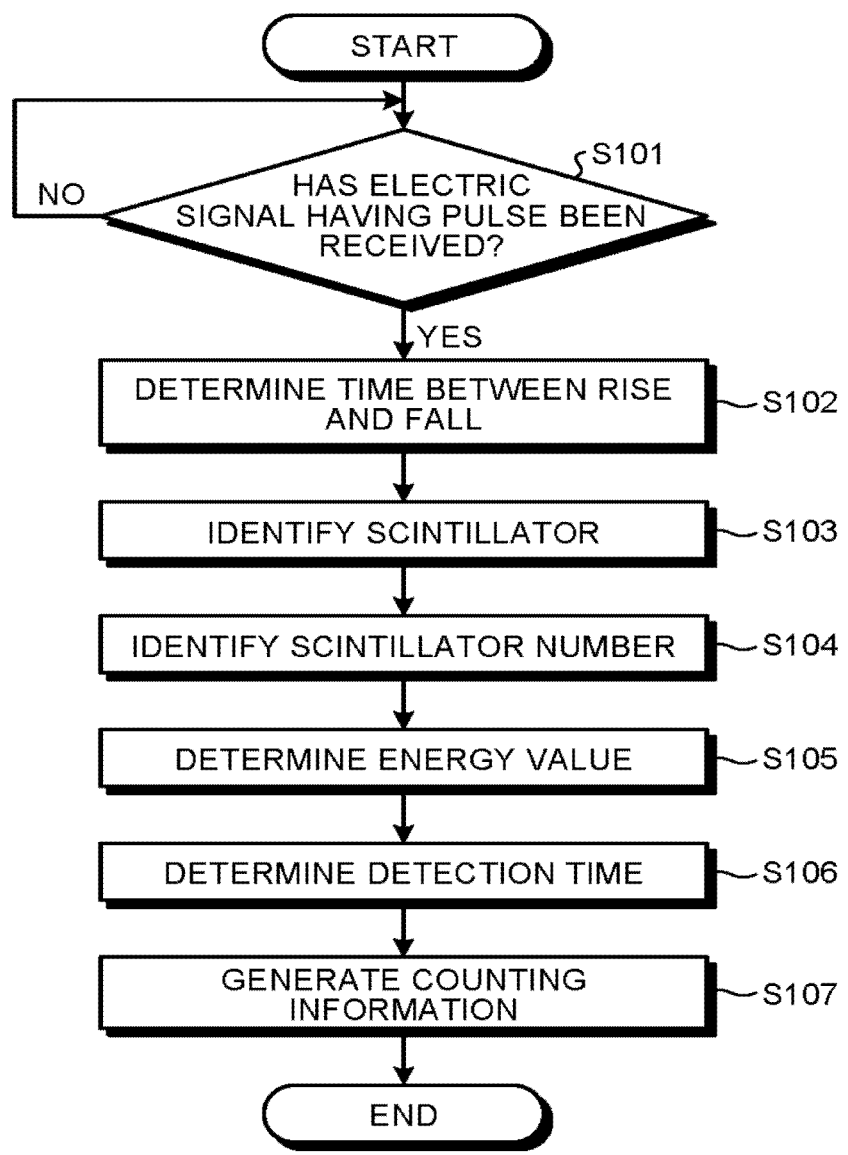
FIG. 10 is a flowchart for illustrating an example of counting information collection processing executed by the counting information collecting unit according to the embodiment.

The following describes a procedure of processing in counting information collection processing executed by the counting information collecting unit 15 according to the embodiment. FIG. 10 is a flowchart for illustrating an example of the counting information collection processing executed by the counting information collecting unit 15 according to the embodiment.

As illustrated in FIG. 10, the identifying unit 15a determines whether the electric signal containing such a pulse as to rise and then fall or such a pulse as to fall and then rise has been received from the differential amplifier circuit 40 (Step S101). If it is determined that the electric signal containing such a pulse as to rise and then fall or such a pulse as to fall and then rise has not been received (No at Step S101), the identifying unit 15a performs the determination processing at Step S101 again.

In contrast, if it is determined that the electric signal containing such a pulse as to rise and then fall or such a pulse as to fall and then rise has been received (Yes at Step S101), the identifying unit 15a determines the time Δt between the rise and the fall of the pulse (Step S102).

The identifying unit 15a, based on the determined Δt and the order of the rise and the fall, identifies the scintillator 14c that has output the light corresponding to the electric signal output from the differential amplifier circuit 40 from among the scintillators 14c (Step S103).

The counting information generating unit 15b identifies the scintillator number (P) indicating the position of the scintillator 14c identified at Step S103 (Step S104).

The counting information generating unit 15b, based on the electric signal output from the differential amplifier circuit 40, calculates the intensity of the electric signal output from the scintillator 14c identified by the identifying unit 15a and integrates the calculated intensity, thereby determining the energy value (E) of the gamma ray made incident on the detector module 14 (Step S105).

The counting information generating unit 15b determines the detection time (T) when the gamma ray has been detected by the detector module 14 (Step S106).

The counting information generating unit 15b then generates the counting information containing the scintillator number (P), the energy value (E), and the detection time (T) (Step S107) and ends the counting information collection processing.

Figure 11:
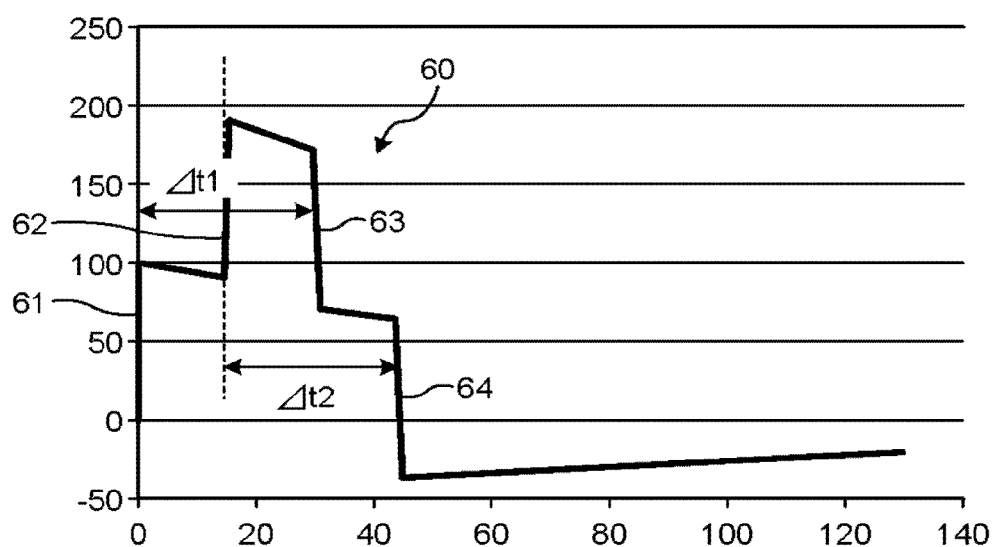
FIG. 11 is a diagram for illustrating a detector module and a PET apparatus according to modification of the embodiment.

The PET apparatus according to the present embodiment has been described. As described above, the detector module 14 and the PET apparatus 100 according to the present embodiment can reduce an increase in the number of the reading channels Modification of Embodiment A pileup may occur in the electric signal output from the SiPM 14d. Given this situation, the following describes an embodiment that can identify the scintillator 14c with high precision even when such a pileup occurs as a modification of the embodiment with reference to FIG. 11. FIG. 11 is a diagram for illustrating the modification of the embodiment.

In the modification of the embodiment, the identifying unit 15a performs processing described below in addition to the processing described in the above embodiment. Specifically, the identifying unit 15a according to the modification determines whether an electric signal containing such a waveform as to rise and then further rise or such a waveform as to fall and then further fall has been received. The electric signal containing such a waveform to rise and then further rise or such a waveform as to fall and then further fall is considered to have a pile up occurring therein.

If it is determined that the electric signal containing such a waveform as to rise and then further rise or such a waveform as to fall and then further fall has been received, it is considered that a pileup is occurring in the received electric signal, and the identifying unit 15a identifies a plurality of groups of corresponding rises and falls from among a plurality of rises and a plurality of falls in the waveform in which the pileup occurs of the received electric signal.

The identifying unit 15a, for example, identifies, from among a first rise, a second rise, . . . , an Nth rise (N is a natural number), a first fall, a second fall, . . . , and an Nth fall, a plurality of groups, that is, a group of the first rise and the first fall, a group of the second rise and the second fall, . . . , and a group of the Nth rise and the Nth fall. The identifying unit 15a thus identifies a plurality of groups of the rise and the fall the number indicating the order of the rise and the fall of which are the same from among the rises and the falls.

When the pileup is occurring as illustrated in the example in FIG. 11, for example, the identifying unit 15a identifies, from among a first rise 61 and a second rise 62 and a first fall 63 and a second fall 64 in a waveform 60 in which the pileup occurs of the received electric signal, a plurality of groups of the rise and the fall the number indicating the order of the rise and the fall of which are the same. In other words, the identifying unit 15a identifies a group of the first rise 61 and the first fall 63 and a group of the second rise 62 and the second fall 64.

The identifying unit 15a, based on times between the rises and the falls indicated by the respective identified groups, identifies the scintillator 14c that has output the light corresponding to the electric signal output from the differential amplifier circuit 40 from among the scintillators 14c. In the example in FIG. 11, for example, the identifying unit 15a determines a time Δt1 between the first rise 61 and the first fall 63 and, based on the determined Δt1, identifies the scintillator 14c that has output the light corresponding to the electric signal output from the differential amplifier circuit 40 from among the scintillators 14c. The identifying unit 15a determines a time Δt2 between the second rise 62 and the second fall 64 and, based on the determined Δt2, identifies the scintillator 14c that has output the light corresponding to the electric signal output from the differential amplifier circuit 40 from among the scintillators 14c.

The modification of the embodiment has been described. The present modification can identify the scintillator 14c that has output light with high precision even when a pileup occurs. The present modification can reduce an increase in the number of the reading channels similarly to the above embodiment.

The following describes a case in which scintillators, a light guide, and photomultiplier tubes (PMTs) are used for a detector of a PET apparatus. In this case, the scintillators convert an incident gamma ray into light and output the light to the PMTs via the light guide. The detector in this case calculates the center of gravity of the pieces of output of the PMTs on which the light has been made incident, thereby calculating the position of a scintillator that has output the light. Such logic for calculating the position of the scintillator is called, for example, the Anger logic. When the position of the scintillator is calculated by the logic, although the number of the PMTs can be smaller than the number of the scintillators, it is necessary to identify the scintillator position from coordinates obtained from a result of the calculation of the center of gravity, and this identification is generally complicated. In addition, there are small numbers of independent channels, and before detection processing to detect one incident gamma ray ends, another gamma ray is made incident, which makes a pileup more likely to occur. When the scintillators, the light guide, and the PMTs are used for the detector, the occurrence of a pileup makes it difficult to identify the scintillator that has output light.

In contrast, as described above, the present modification can identify the scintillator 14c that has output light with high precision even when a pileup occurs.

The functions exerted by the detector module 14 and the counting information collecting unit 15 in the above embodiment or the modification thereof can be exerted by other nuclear medical imaging apparatuses such as a single photon emission computed tomography (SPECT) apparatus, a PET-CT apparatus, a SPECT-CT apparatus, and a PET-MRI apparatus. The PET-CT apparatus, for example, may include the detector module 14 and the counting information collecting unit 15 in the above embodiment or the modification thereof and a gantry for CT that collects data for use in reconstruction of X-ray CT images. The following describes a configuration of such a PET-CT apparatus with reference to FIG. 12.

Figure 12:
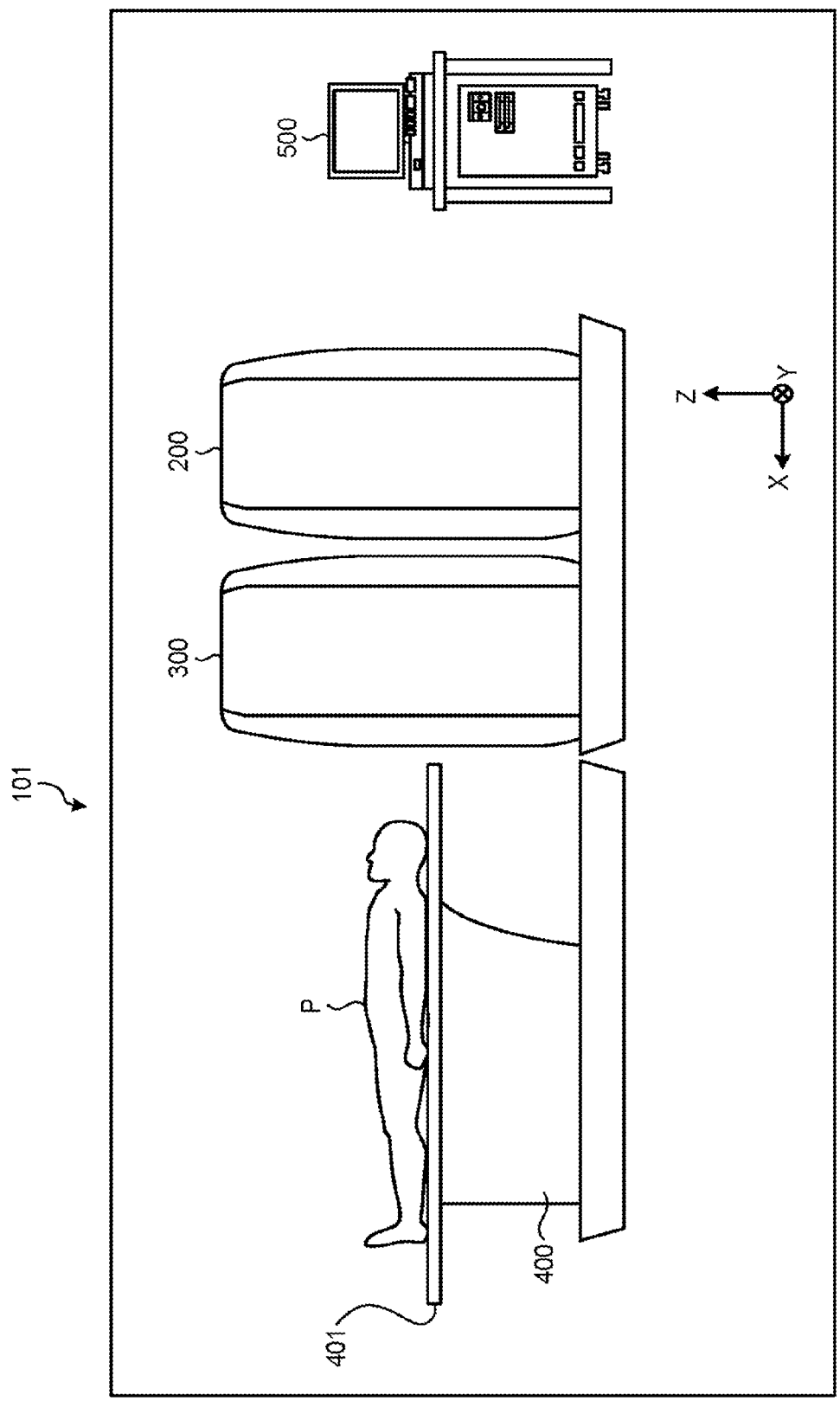
FIG. 12 is a diagram illustrating an example of a configuration of a PET-CT apparatus.

FIG. 12 is a diagram illustrating an example of a configuration of a PET-CT apparatus 101. As illustrated in FIG. 12, the PET-CT apparatus 101 according to the present embodiment includes a gantry 200 for PET, a gantry 300 for X-ray CT, a couch 400, and a console apparatus 500. As illustrated in FIG. 12, the couch 400 includes a couchtop 401 on which the subject P is mounted and moves the subject P into an imaging port of the PET-CT apparatus 101 under the control of the console apparatus 500. The subject P is not included in the PET-CT apparatus 101.

The gantry 200 for PET detects annihilation gamma rays emitted from the subject P using the detector modules 14 arranged around the subject P in a ring shape and generates counting information based on the detection result.

Figure 13:
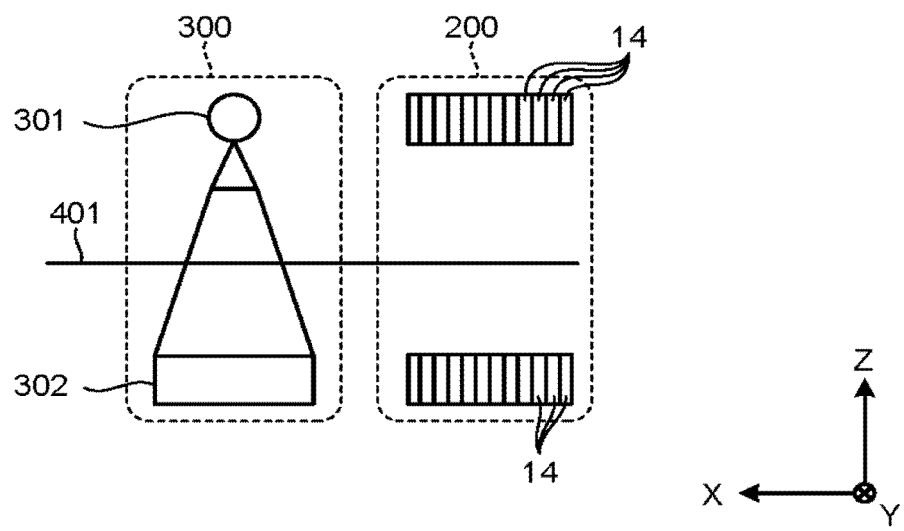
FIG. 13 is a diagram illustrating the gantry for PET and the gantry for X-ray CT.
Figure 14:
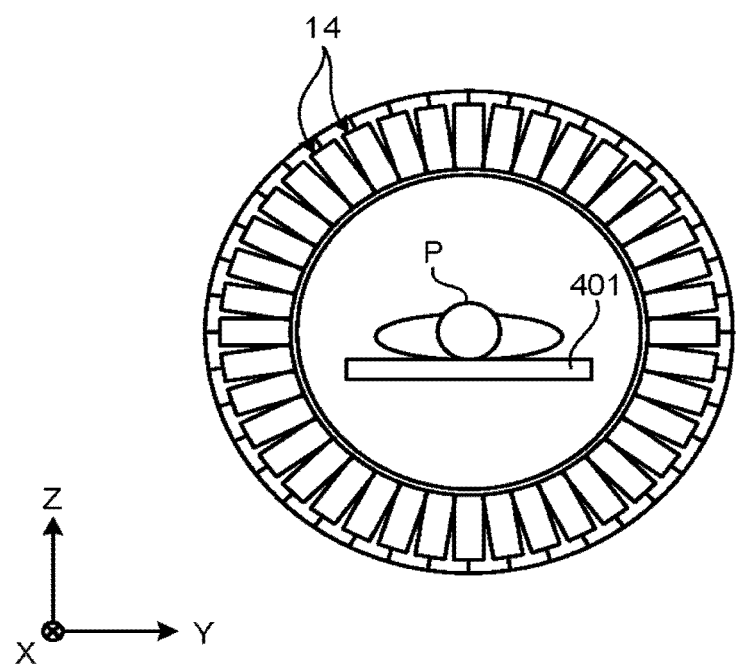
FIG. 14 is a diagram illustrating a configuration of the gantry for PET.

FIG. 13 is a diagram illustrating the gantry 200 for PET and the gantry 300 for X-ray CT. FIG. 14 is a diagram illustrating a configuration of the gantry 200 for PET. As illustrated in FIG. 13 and FIG. 14, in the gantry 200 for PET, a plurality of detector modules 14 are arranged in an X-axial direction, and a plurality of detector modules 14 are arranged around the subject P in a ring shape.

The gantry 300 for X-ray CT detects X-rays having passed through the subject P and generates projection data based on the detection result. As illustrated in FIG. 13, for example, the gantry 300 for X-ray CT includes an X-ray tube 301 that emits X-rays and an X-ray detector 302 that detects the X-rays emitted by the X-ray tube 301. While the X-ray tube 301 and the X-ray detector 302 rotate about the body axis of the subject P, the X-ray tube 301 irradiates the subject P with the X-rays, and the X-ray detector 302 detects the X-rays having passed through the subject P. The gantry 300 for X-ray CT performs amplification processing, analog to digital (AD) conversion processing, or e like on the X-rays detected by the X-ray detector 302 to generate the projection data.

Figure 15:
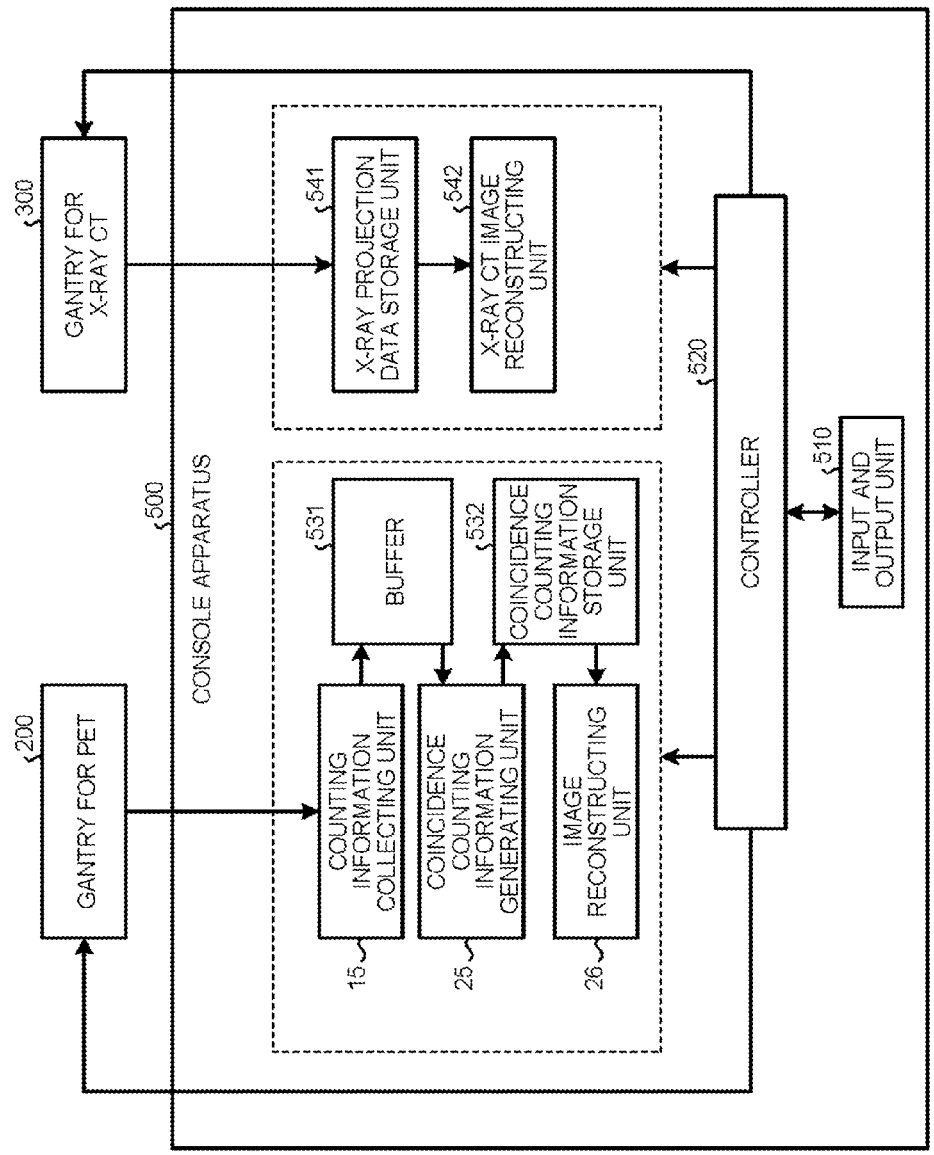
FIG. 15 is a diagram illustrating a configuration of the console apparatus of an embodiment.

FIG. 15 is a diagram illustrating a configuration of the console apparatus 500 of the present embodiment. The console apparatus 500 generates coincidence counting information using the counting information generated by the gantry 200 for PET and reconstructs PET images based on the generated coincidence counting information. The console apparatus 500 reconstructs X-ray CT images based on the projection data generated by the gantry 300 for X-ray CT.

As illustrated in FIG. 15, for example, the console apparatus 500 includes an input and output unit 510 and a controller 520. The console apparatus 500 includes a buffer 531, a coincidence counting information storage unit 532, the counting information collecting unit 15, the coincidence counting information generating unit 25, and the image reconstructing unit 26. The console apparatus 50 includes an X-ray projection data storage unit 541 and an X-ray CT image reconstructing unit 54. Although the present embodiment describes a case in which the reconstruction of PET images and the reconstruction of X-ray CT images are performed by physically one console apparatus, the reconstruction of PET images and the reconstruction of X-ray CT images may be performed by separate console apparatuses.

The input and output unit 510 receives various kinds of instructions from a user of the PET-CT apparatus 101 and transmits the received various kinds of instructions to the controller 520. The input and output unit 510 receives information from the controller 520 and outputs the received information. The input and output unit 510 is, for example, an input unit such as a keyboard, a mouse and a microphone and an output unit (also referred to as display unit) such as a monitor and a speaker.

The controller 520 controls the gantry 200 for PET and the gantry 300 for X-ray CT, thereby controlling imaging by the PET-CT apparatus 101. The controller 520 controls PET image reconstruction processing and X-ray CT image reconstruction processing in the console apparatus 500. The controller 520 outputs PET images, X-ray CT images, or the like to the monitor or the like of the input and output unit 510. The controller 520 is an electronic circuit such as an application specific integrated circuit (ASIC), a field programmable gate array (FPGA), a central processing unit (CPU), and a micro processing unit (MPU).

The buffer 531 stores therein counting information stored by the counting information collecting unit 15. The coincidence counting information storage unit 532 stores therein coincidence counting information stored by the coincidence counting information generating unit 25. The buffer 531 and the coincidence counting information storage unit 53 are, for example, semiconductor memory elements such as a random access memory (RAM) and a flash memory, hard disks, and optical discs.

The counting information collecting unit 15 generates counting information from output signals of the detector modules 14 of the gantry 200 for PET and stores the generated counting information in the buffer 531. The counting information collecting unit 15 may be installed within the gantry 200 for PET.

The coincidence counting information generating unit 25 generates a time-series list of coincidence counting information using the counting information collected by the counting information collecting unit 15. Specifically, the coincidence counting information generating unit 25 searches the counting information stored in the buffer 531 for a group of the counting information that has counted a pair of annihilation gamma rays substantially simultaneously based on the detection time of the counting information. The coincidence counting information generating unit 25 generates the coincidence counting information for each group of the counting information searched for and stores the generated coincidence counting information in the coincidence counting information storage unit 532 while arranging the information generally on a time-series basis.

The image reconstructing unit 26 reconstructs PET images. Specifically, the image reconstructing unit 26 reads the time-series list of the coincidence counting information stored in the coincidence counting information storage unit 532 as projection data and reconstructs the PET images using the read projection data.

The X-ray projection data storage unit 541 stores therein projection data transmitted from the gantry 300 for X-ray CT. The X-ray CT image reconstructing unit 542 performs back projection processing on the projection data stored in the X-ray projection data storage unit 541 by, for example, the filtered back projection (FBP) method, thereby reconstructing X-ray CT images.

The PET-CT apparatus 101 includes the detector modules 14 in the above embodiment or the modification thereof and can reduce an increase in the number of the reading channels.

The PET-MRI apparatus may include the detector module 14 and the counting information collecting unit 15 in the above embodiment or the modification thereof and a gantry for MRI that collects magnetic resonance signals. The following describes a configuration of such a PET-MRI apparatus with reference to FIG. 16.

Figure 16:
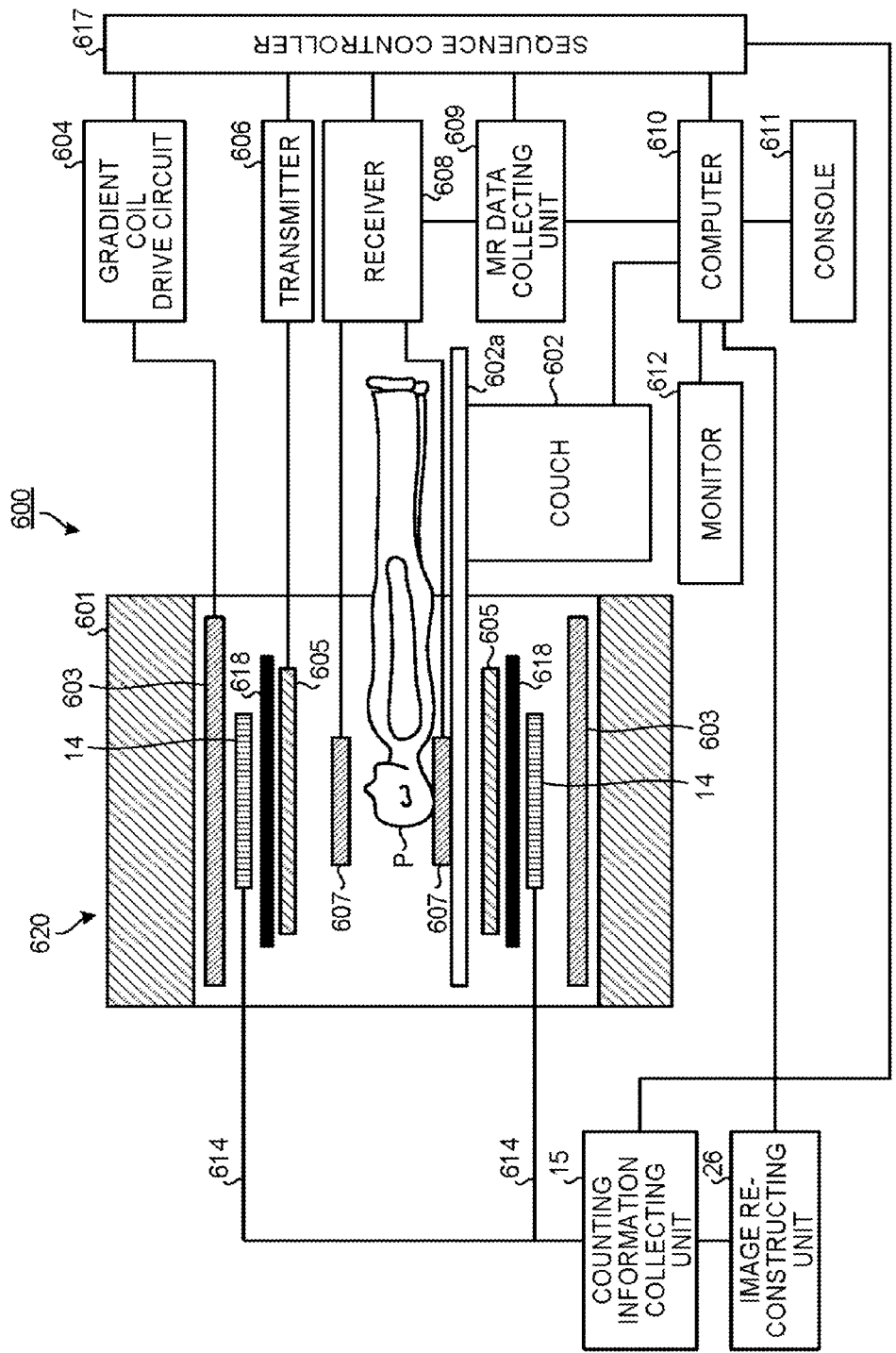
FIG. 16 is a diagram illustrating a configuration of a PET-MRI apparatus.

FIG. 16 is a diagram illustrating a configuration of a PET-MRI apparatus 600. As illustrated in FIG. 16, the PET-MRI apparatus 600 includes the counting information collecting unit 15, the image reconstructing unit 26, a couch 602, a gradient coil drive circuit 604, a transmitter 606, a receiver 608, an MRI data collecting unit 609, a computer 610, a console apparatus 611, a monitor 612, a signal line 614, a sequence controller 617, and a gantry 620 for MRI.

The gantry 620 for MRI includes a static magnetic field magnet 601, a gradient coil 603, a high-frequency coil 605 for transmission, a high-frequency coil 607 for reception, detector modules 14, and a high-frequency shield 618.

The static magnetic field magnet 601 generates a static magnetic field within a substantially cylindrical bore. The bore is formed as an inner wall of the substantially cylindrical gantry that houses therein the static magnetic field magnet 601, the gradient coil 603, and the like. The couch 602 has a couchtop 602a on which the subject P is mounted. At the time of imaging, the couch 602 moves the couchtop 602a into the bore to move the subject P into the static magnetic field.

The gradient coil 603 applies gradient magnetic fields Gx, Gy, and Gz the magnetic field strength of which linearly change in X, Y, and Z directions, respectively, to the subject P. The gradient coil 603 is formed in a substantially cylindrical shape and is arranged on the inner circumferential side of the static magnetic field magnet 601. The gradient coil drive circuit 604 drives the gradient coil 603 under the control of the sequence controller 617.

The high-frequency coil 605 for transmission applies a high-frequency magnetic field to the subject P placed within the static magnetic field based on a high-frequency pulse transmitted from the transmitter 606. The high-frequency coil 605 for transmission is formed in a substantially cylindrical shape and is arranged on the inner circumferential side of the gradient coil 603. The transmitter 606 transmits the high-frequency pulse to the high-frequency coil 605 for transmission under the control of the sequence controller 617.

The high-frequency coil 607 for reception detects magnetic resonance signals emitted from the subject P through the application of the high-frequency magnetic field and a gradient magnetic field. The high-frequency coil 607 for reception is, for example, a surface coil arranged on the surface of the subject P in accordance with a site to be imaged. When the body part of the subject P is imaged, for example, two reception high-frequency coils 607 are arranged above and below the subject. The receiver 608 receives the magnetic resonance signals detected by the high-frequency coil 607 for reception under the control of the sequence controller 617. The receiver 608 sends the received magnetic resonance signals to the MR data collecting unit 609.

The MR data collecting unit 609 collects the magnetic resonance signals sent from the receiver 608 under the control of the sequence controller 617. The MR data collecting unit 609 amplifies, detects, and then A/D converts the collected magnetic resonance signals and sends the magnetic resonance signals to the computer 610. The computer 610 is controlled by the console apparatus 611 and reconstructs MR images based on the magnetic resonance signals sent from the MR data collecting unit 609. The computer 610 causes the monitor 612 to display the reconstructed MR images.

The detector modules 14 are arranged so as to surround the subject P in a ring shape. The detector modules 14 convert gamma rays emitted from within the subject P into light and convert the converted light into electric signals. The detector module 14 send the electric signals to the counting information collecting unit 15 via the signal line 614.

The counting information collecting unit 15 generates coincidence counting information under the control of the sequence controller 617. The counting information collecting unit 15, for example, generates counting information from the output signals of the detector modules 14 similarly to the first embodiment. The counting information collecting unit 15 generates a time-series list of coincidence counting information based on the generated counting information.

The image reconstructing unit 26 reconstructs PET images using the time-series list of the coincidence counting information generated by the counting information collecting unit 15 as projection data. The PET images reconstructed by the image reconstructing unit 26 are transmitted to the computer 610 and are displayed on the monitor 612. The sequence controller 617 receives various kinds of sequence information to be executed at the time of imaging from the computer 610 and controls the above-described units.

The PET-MRI apparatus 600 include the detector modules 14 in the above embodiment or the modification thereof and can reduce an increase in the number of the reading channels.

The detector module 14 may include the functions of the identifying unit 15a and the counting information generating unit 15b of the counting information collecting unit 15.

The detector module 14 and the PET apparatus 100 of at least one of the embodiments described above can reduce an increase in the number of the reading channels.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A detector, comprising:
   a plurality of scintillators each configured to convert a gamma ray into light and to output the light;
   a plurality of photomultipliers each configured to convert the light output from each of the scintillators into an electric signal and to output the electric signal, the respective photomultipliers being optically coupled to the respective scintillators;
   a signal line having a first path and a second path through which the electric signal passes, wherein the first path and the second path have different lengths for each of the photomultipliers;
   identifying circuitry configured to identify the photomultiplier that outputs the electric signal by a time difference between the electric signal passing through the first path and the electric signal passing through the second path; and
   counting information generating circuitry configured to generate counting information according to the identified photomultiplier.

2. A nuclear medical imaging apparatus, comprising:
   a detector that comprises
      a plurality of scintillators each configured to convert a gamma ray into light and to output the light;
      a plurality of photomultipliers each configured to convert the light output from each of the scintillators into an electric signal and to output the electric signal, the respective photomultipliers being optically coupled to the respective scintillators; and
      a signal line having a first path and a second path through which the electric signal passes, wherein the first path and the second path have different lengths for each of the photomultipliers;
      identifying circuitry configured to identify the photomultiplier that outputs the electric signal by a time difference between the electric signal passing through the first path and the electric signal passing through the second path; and
      counting information generating circuitry configured to generate counting information according to the identified photomultiplier, wherein
   based on the time difference between the electric signal passing through the first path and the electric signal passing through the second path, the identifying circuitry is configured to identify a scintillator that has output light corresponding to the electric signal passing through the first path and the electric signal passing through the second path from among the scintillators.

3. The nuclear medical imaging apparatus according to claim 2, wherein the time difference is based on a time between a rise and a fall in a differential signal between the electric signal passing through the first path and the electric signal passing through the second path.

4. The nuclear medical imaging apparatus according to claim 3, wherein further based on a time sequence order of the rise and fall in the differential signal, the identifying circuitry is configured to identify the scintillator.

5. The nuclear medical imaging apparatus according to claim 3, wherein when a pileup occurs in the differential signal, the identifying circuitry is configured to identify a plurality of groups of corresponding rises and falls from among a plurality of rises and a plurality of falls in the differential signal and, based on times between the rises and the falls indicated by the respective identified groups, identify the scintillator that has output the light corresponding to the differential signal from among the scintillators.

6. A positron emission tomography-computed tomography (PET-CT) apparatus comprising:
   a detector that comprises
      a plurality of scintillators each configured to convert a gamma ray into light and to output the light;
      a plurality of photomultipliers each configured to convert the light output from each of the scintillators into an electric signal and to output the electric signal, the respective photomultipliers being optically coupled to the respective scintillators;
      a signal line having a first path and a second path through which the electric signal passes, wherein the first path and the second path have different lengths for each of the photomultipliers;
      identifying circuitry configured to identify the photomultiplier that outputs the electric signal by a time difference between the electric signal passing through the first path and the electric signal passing through the second path; and
      counting information generating circuitry configured to generate counting information according to the identified photomultiplier; and
   a gantry for CT configured to collect data for use in reconstruction of X-ray CT images.

7. A positron emission tomography-magnetic resonance imaging (PET-MRI) apparatus comprising:
   a detector that comprises:
      a plurality of scintillators each configured to convert a gamma ray into light and to output the light;
      a plurality of photomultipliers each configured to convert the light output from each of the scintillators into an electric signal and to output the electric signal, the respective photomultipliers being optically coupled to the respective scintillators:
      a signal line having a first path and a second path through which the electric signal passes, wherein the first path and the second path have different lengths for each of the photomultipliers;
      identifying circuitry configured to identify the photomultiplier that outputs the electric signal by a time difference between the electric signal passing through the first path and the electric signal passing through the second path; and
      counting information generating circuitry configured to generate counting information according to the identified photomultiplier; and
   a gantry for MRI configured to collect magnetic resonance signals.

* * * * *